(12) United States Patent
Jones et al.

(10) Patent No.: US 11,850,586 B2
(45) Date of Patent: Dec. 26, 2023

(54) ANALYTE SENSOR PACKAGE AND METHOD FOR ANALYZING FLUID SAMPLES

(71) Applicant: Maxim Integrated Products, Inc., San Jose, CA (US)

(72) Inventors: Joy T. Jones, San Jose, CA (US); Ronald B. Koo, Los Altos, CA (US); Paul G. Schroeder, San Jose, CA (US); Albert Song, San Jose, CA (US); Sudarsan Uppili, Portland, OR (US); Xiaoming Yan, Campbell, CA (US); Qi Luo, San Jose, CA (US); Sean Cahill, Palo Alto, CA (US)

(73) Assignee: MAXIM INTEGRATED PRODUCTS, INC., San Jose, CA (US)

( * ) Notice: Subject to any disclaimer, the term of this patent is extended or adjusted under 35 U.S.C. 154(b) by 846 days.

(21) Appl. No.: 16/634,391

(22) PCT Filed: Jul. 27, 2018

(86) PCT No.: PCT/US2018/044197
§ 371 (c)(1),
(2) Date: Jan. 27, 2020

(87) PCT Pub. No.: WO2019/023646
PCT Pub. Date: Jan. 31, 2019

(65) Prior Publication Data
US 2020/0171495 A1 Jun. 4, 2020

Related U.S. Application Data

(60) Provisional application No. 62/537,672, filed on Jul. 27, 2017.

(51) Int. Cl.
*B01L 3/00* (2006.01)

(52) U.S. Cl.
CPC .... *B01L 3/502715* (2013.01); *B01L 3/502707* (2013.01); *B01L 2300/0636* (2013.01); *B01L 2300/0645* (2013.01)

(58) Field of Classification Search
CPC ......... B01L 3/502715; B01L 3/502707; B01L 2300/0636; B01L 2300/0645;
(Continued)

(56) References Cited

U.S. PATENT DOCUMENTS 7,172,897 B2 * 2/2007 Blackburn ............ B01L 3/5027
204/406
9,670,445 B1 6/2017 Kuo et al.
(Continued)

FOREIGN PATENT DOCUMENTS

DE 102016108413 A1 11/2016
DE 102016116264 A1 3/2017
(Continued)

OTHER PUBLICATIONS

Jia et al. "Electrically conductive composites based on epoxy resin containing polyaniline-DBSA- and polyaniline-DBSA-coated glass fibers" Journal of Applied Polymer Science, vol. 91, 1329-1334 (Year: 2004).*
(Continued)

*Primary Examiner* — Brian R Gordon
(74) *Attorney, Agent, or Firm* — Kevin E. West; Advent, LLP

(57) ABSTRACT

A sensor package, a sensor system, and a method for fabricating the sensor package are described that include a sensing chip having dispense chemistry disposed over an array of conductive elements. In an implementation, the sensor package may include a sensing chip that may include at least one conductive element, wherein the at least one conductive element may be part of an array of conductive
(Continued)

elements defining a M by N matrix, where M is a number of rows of the at least one conductive element and N is a number of columns of the at least one conductive element. The sensing chip may further include dispense chemistry that may be disposed on the at least one conductive element and at least one contact pad. The sensor package may further include a microfluidic cap that may be positioned over at least a portion of the sensing chip, wherein the microfluidic cap and the sensing chip may define a cavity that may be configured to receive a fluid sample. The microfluidic cap may further include at least one electrode that may be configured to sense an analyte in the fluid sample. The at least one electrode may be coupled to the at lease one contact pad of the sensing chip via a conductive adhesive.

14 Claims, 9 Drawing Sheets

(58) Field of Classification Search
CPC . H01L 2224/05553; H01L 2224/48091; H01L 2224/49171; H01L 23/00; H01L 2924/16235; A61B 5/1468; A61B 5/14507; A61B 5/14532; A61B 5/14546; A61B 5/145
See application file for complete search history.

(56) References Cited

U.S. PATENT DOCUMENTS

| | | |
|---|---|---|
| 9,753,028 B2 | 9/2017 | Koo et al. |
| 10,107,790 B1 | 10/2018 | Koo et al. |
| 10,436,775 B2 | 10/2019 | Koo et al. |
| 10,520,487 B2 | 12/2019 | Koo et al. |
| 10,605,816 B1 | 3/2020 | Koo et al. |
| 11,351,548 B2 * | 6/2022 | Jones .................. B81C 1/00309 |
| 11,365,386 B2 * | 6/2022 | Gosselin ................ C12M 23/12 |
| 2004/0086869 A1 * | 5/2004 | Schembri ............. B01J 19/0046 506/9 |
| 2006/0194331 A1 * | 8/2006 | Pamula ................. B81B 3/0021 422/400 |
| 2010/0089135 A1 | 4/2010 | De Langen et al. |
| 2010/0171189 A1 | 7/2010 | Liu |
| 2013/0168250 A1 * | 7/2013 | Fogleman ............... G01F 22/00 204/549 |
| 2015/0346131 A1 | 12/2015 | Mohseni et al. |
| 2016/0199832 A1 * | 7/2016 | Jamshidi ............. B01F 33/3031 204/600 |
| 2016/0363550 A1 | 12/2016 | Koo et al. |
| 2018/0104694 A1 * | 4/2018 | Huff .................. B01L 3/502784 |
| 2018/0111126 A1 * | 4/2018 | Osmus ................. G01N 33/573 |
| 2018/0126381 A1 * | 5/2018 | Huff ............. G01N 27/44721 |
| 2018/0207640 A1 * | 7/2018 | Hayden ............ G01N 33/54373 |
| 2019/0090801 A1 * | 3/2019 | Rogers ................. A61B 5/6868 |
| 2019/0111420 A1 * | 4/2019 | Jones .................... B81B 7/0061 |
| 2019/0113475 A1 * | 4/2019 | Fan ................... B01L 3/502753 |
| 2020/0319135 A1 * | 10/2020 | Fan ................... H01L 21/02172 |

FOREIGN PATENT DOCUMENTS

| | | |
|---|---|---|
| KR | 20130099648 A | 9/2013 |
| KR | 20140120138 A | 10/2014 |
| WO | 2016161400 A1 | 10/2016 |
| WO | 2017124104 A1 | 7/2017 |

OTHER PUBLICATIONS

Burdallo et al. "Integration of microelectronic chips in microfluidic systems on printed circuit board" 2012 J. Micromech. Microeng. 22 105022 (Year: 2012).*
International Search Report and the Written Opinion for Application No. PCT/US2018/044197, dated Jan. 31, 2019, 7 Pages.

* cited by examiner

ANALYTE SENSOR PACKAGE AND METHOD FOR ANALYZING FLUID SAMPLES

The present application claims the benefit under 35 U.S.C. § 119(e) of U.S. Provisional Application Ser. No. 62/537,672, entitled "Analyte sensor package and method for analyzing fluid samples," filed Jul. 27, 2017. The above-referenced Provisional Application is herein incorporated by reference in its entirety.

BACKGROUND

The analysis of components in biological fluids (e.g., blood, urine, saliva, etc.) and other fluids (e.g., liquid or gas samples, etc.) is continuing to increase in importance. Biological fluid tests can be used in a health care environment to determine physiological and/or biochemical states, such as disease, mineral content, pharmaceutical drug effectiveness, and/or organ function. For example, it may be desirable to determine an analyte concentration within an individual's blood to manage a health condition, such as diabetes. Consequently, the individual may be required to go to a diagnostic laboratory or medical facility to have blood drawn and then wait (often for an extended period) for analysis results, which can be inconvenient. The individual must often schedule a follow-up visit with a healthcare provider to review the analysis results, which can also add cost. For these reasons and others, there is an increasing need for devices that can facilitate onsite (e.g., point-of-need) testing.

DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

DETAILED DESCRIPTION

Overview

Figure 1A:
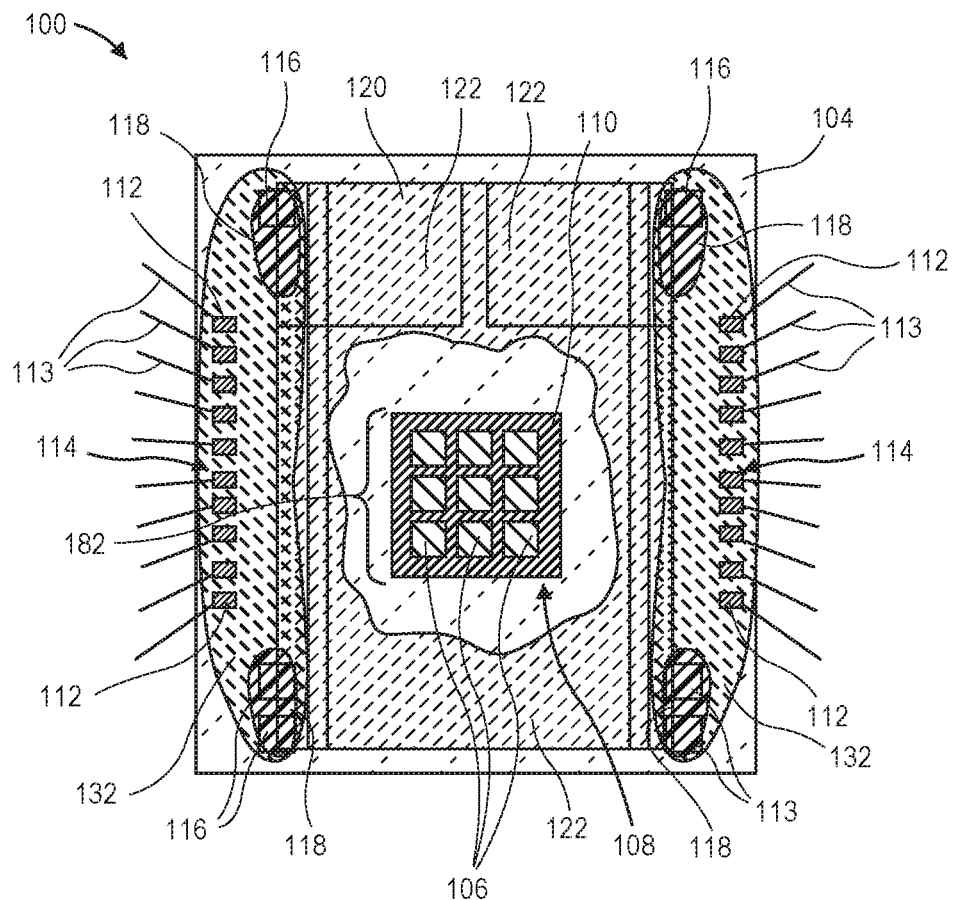
FIG. 1A is a partial top plan view illustrating an embodiment of a sensor chip and sensor package having an array of conductive elements with dispense chemistry disposed on the array of conductive elements, in accordance with an example implementation of the present disclosure.

Sensor systems that allow for onsite analysis of fluid samples (e.g., biological fluids or other liquid or gas samples) are increasing in importance. For example, onsite sensor systems can be used to analyze freshly collected fluid samples rather than having to preserve the fluid samples for transport to a remotely located lab for analysis. Onsite sensor systems can also be used to obtain faster results for analyzed fluid samples, to perform analysis of fluid samples in remote areas where transportation and/or access to test equipment may be limited, to perform self-tests for patients who may need to have one or more of their biological samples (e.g., blood, saliva, urine, etc.) analyzed frequently (rather than having to go to a healthcare facility each time a test is needed), and so forth.

Accordingly, a sensor package, a sensor system, and a method for fabricating the sensor package are described that may include a sensing chip having dispense chemistry disposed over an array of conductive elements. In an example implementation, the sensor package may include a sensing chip, where the sensing chip may include at least one conductive element. In some examples, the at least one conductive element may be disposed on and/or proximate to a center of the sensing chip and may be part of an array forming an M by N matrix, where M is a number of rows of conductive elements and N is a number of columns of conductive elements. The sensing chip may further include dispense chemistry that may be disposed on the at least one conductive element and at least one contact pad. Additionally, a microfluidic cap may be positioned over at least a portion of the sensing chip. The microfluidic cap and the sensing chip may define a cavity that may be configured to receive a fluid sample. The microfluidic cap may include at least one electrode that may be configured to sense an analyte in the fluid sample. The at least one electrode may be coupled to the at least one contact pad of the sensing chip via a conductive adhesive.

In another example implementation of the disclosure, a sensor system may include a base substrate and a sensor package coupled to the base substrate. In an example implementation, the sensor package may include a sensing chip, where the sensing chip may include at least one conductive element. In some examples, the at least one conductive element may be disposed on and/or proximate to a center of the sensing chip and may be part of an array forming an M by N matrix, where M is a number of rows of conductive elements and N is a number of columns of conductive elements. The sensing chip may further include dispense chemistry that may be disposed on the at least one conductive element and at least one contact pad. Additionally, a microfluidic cap may be positioned over at least a portion of the sensing chip. The microfluidic cap and the sensing chip may define a cavity that may be configured to receive a fluid sample. The microfluidic cap may include at least one electrode that may be configured to sense an analyte in the fluid sample. The at least one electrode may be coupled to the at least one contact pad of the sensing chip via a conductive adhesive.

In another example implementation of the disclosure, a method for fabricating the sensor package may include placing dispense chemistry on at least one conductive element of a sensing chip, wherein the at least one conductive element is part of an array of conductive elements defining a M by N matrix, where M is a number of rows of the at least one conductive element and N is a number of columns of the at least one conductive element, and wherein the sensing chip may further include at least one contact pad. The method may further include placing a conductive adhesive on the at least one contact pad. The method may further include determining an upper interlayer dielectric of the sensing chip and at least one electrode formed on a microfluidic cap comprise substantially planar surfaces. The method may further include positioning the microfluidic cap over at least a portion of the sensing chip. The microfluidic cap and the sensing chip may define a cavity that may be configured to receive a fluid sample. placing a microfluidic cap on the adhesive and the sensing chip. The method may further include coupling the at least one electrode to the at least one contact pad via the conductive adhesive.

Example Implementations

FIGS. 1A through 1I illustrate a sensor package 100 and a sensor system 102 that may be configured to analyze a fluid sample in accordance with an example implementation of the present disclosure. In some instances, the sensor package 100 and/or the sensor system 102 may be utilized as a test strip or may be coupled to and/or embedded within a different device. For example, the sensor package 100 and/or sensor system 102 can be coupled to and/or embedded within a mobile device (e.g., a smartphone, a wearable device, a tablet, a digital camera, a notebook computer, a media player, a portable gaming device, and so forth), a computer, an analysis instrument, and so forth. In other example embodiments, the sensor package 100 and/or the sensor system 102 may be a standalone device. The sensor package 100 and/or the sensor system 102 can be configured to analyze the fluid sample by scanning the fluid sample to generate a signal (e.g., a digital signal, an electrical signal, and so on) that may be used to detect at least one analyte in the fluid sample and/or determine at least one characteristic (e.g., an amount, spatial distribution, dimension, concentration, etc.) of one or more particles (e.g., cells, biological structures, beads, microparticles, etc.) in the fluid sample.

The sensor package 100 and sensor system 102 described herein may include a sensing chip 104. The sensing chip 104 may include an array of at least one conductive element 106, which may be disposed on and/or proximate to a center 108 of the sensing chip 104, and a microfluidic cap 120 that may be disposed on and/or over the sensing chip 104. The at least one conductive element 106 may include an array of conductive elements by itself or it may include a single conductive element, as illustrated in FIGS. 1A through 1I. The at least one conductive element 106 can include a first top conductive layer 166 and/or a second top conductive layer 168, which are further described with reference to FIGS. 1H and 1I. It may be appreciated that the lateral and cross-sectional dimensions illustrated in FIG. 1A through 1I are for illustrative purposes only and may not be necessarily to scale. In some example embodiments of the disclosure, the lateral dimensions may be close to scale, but cross-sectional dimensions may not be to scale.

As illustrated in FIGS. 1A through 1I, the sensor package 100 may include a sensing chip 104. As it will be apparent from the embodiments illustrated in FIGS. 1H and 1I, the sensing chip 104 may include a plurality of conductive layers, a plurality of interlayer dielectrics or one or more top or upper inter layer dielectrics. In these embodiments, the conductive layer(s) can include conductive traces (e.g., a metal trace), conductive lines (e.g., metal lines), redistribution layers, conductive vias between conductive layers (e.g., metal-filled vias), and so forth. It is contemplated that the conductive layers can include a variety of materials and/or combinations of metals. Additionally, the interlayer dielectric(s) can include a variety of materials and/or combinations of dielectric and/or non-conductive materials. Some examples of an interlayer dielectric can include a polymer (e.g., an epoxy), silicon dioxide (e.g., $SiO_2$), silicon nitride (e.g., $SiN_x$), and so forth. It is contemplated that other materials, combinations of materials, and/or configurations for the conductive layers and/or the several interlayer dielectrics can be utilized.

In the example embodiments illustrated in FIGS. 1A through 1I, the sensing chip 104 can include at least one metal panel 106 (e.g., an array of conductive elements 106 that may be arranged as an M×N (or M by N) matrix 182 and on and/or proximate to a center 108 of the sensing chip 104, the first top conductive layer 166, the second top conductive layer 168). The sensing chip 104 may further include dispense chemistry 110 that may be disposed on/over the at least one conductive panel 106. The sensing chip 104 may further include at least one bonding pad 112, and/or at least one contact pad 116. When an M×N matrix 182 configuration is utilized, M can be a number of rows of conductive elements 106 and N can be a number of columns of conductive elements 106. Although a rectangular arrangement of the conductive elements 106 is illustrated in FIG. 1A through 1I, the M×N matrix 182 of conductive elements 106 can include other configurations (e.g., a non-rectangular geometric layout, such as a square configuration, a circular configuration, an irregular configuration). In an example embodiment of the disclosure, at least one conductive element 106 in the M×N matrix 182 can include a dummy element (not shown) (e.g., electrically or not electrically coupled to the adhesive 118 and/or the sensing chip 104). For example, the M×N matrix 182 can include at least one column and/or row of dummy elements. In implementations, the dummy element(s) may be coupled to an alternating current (AC) ground and/or other electric potential. In these implementations, the dummy element(s) may not function as a sensing element (e.g., conductive element 106) that senses an analyte/sample exposed to the sensing chip 104. In other example embodiments, the dummy element(s) may not provide any sensing function but may be incorporated in order to allow additional conductive elements 106 to be added later or to incorporate other functionality in the sensor package 100 at a future time.

As depicted in FIGS. 1A through 1D, the sensor package 100 may include an adhesive 118 that may be coupled to at least one contact pad 116 that may be disposed on the sensing chip 104. The at least one contact pad 116 can be coupled to active circuitry within the sensing chip 104. Some examples of an adhesive 118 may include a conductive adhesive (e.g., an electrically conductive epoxy) that may be configured to mechanically and/or electrically couple the contact pad 116 to another electrical component of the sensor package 100, such as an electrode 122. Other examples of an adhesive may include a non-conductive adhesive (e.g., an epoxy). In some embodiments, the adhesive 118 may include glass fibers and/or beads, which may serve to control a gap between the microfluidic cap 120 and the sensing chip 104. In an example implementation, the at least one contact pad 116 may be disposed on the sensing chip 104 proximate to the at least one metal panel 106. In other example embodiments, the at least one contact pad 116 may be disposed on the sensing chip 104 proximate to an outer edge or periphery 114. The at least one contact pad 116 can include a variety of conductive material, such as copper, aluminum, tungsten, and so on.

Figure 1B:
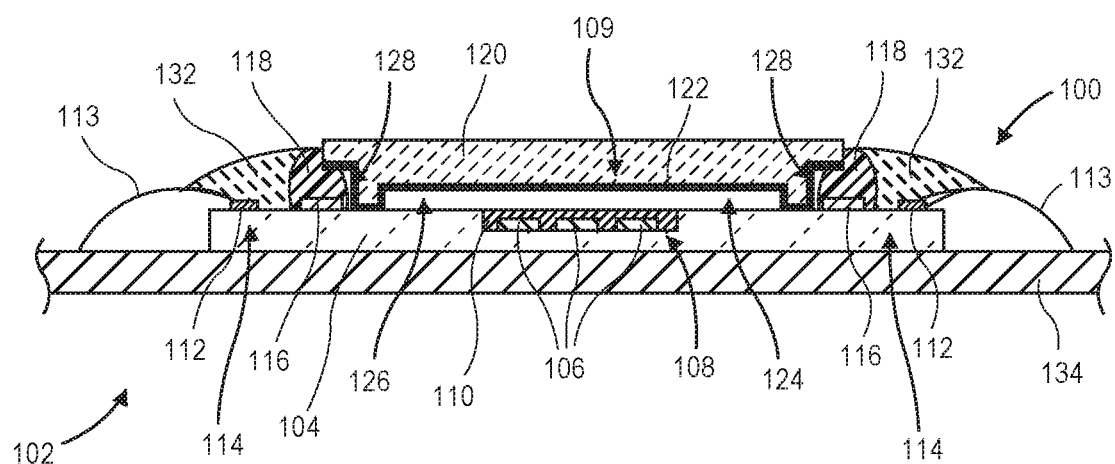
FIG. 1B is a cross-sectional side view illustrating an embodiment of a sensor chip and sensor package having an array of conductive elements with dispense chemistry disposed on the array of conductive elements, in accordance with an example implementation of the present disclosure.
Figure 1C:
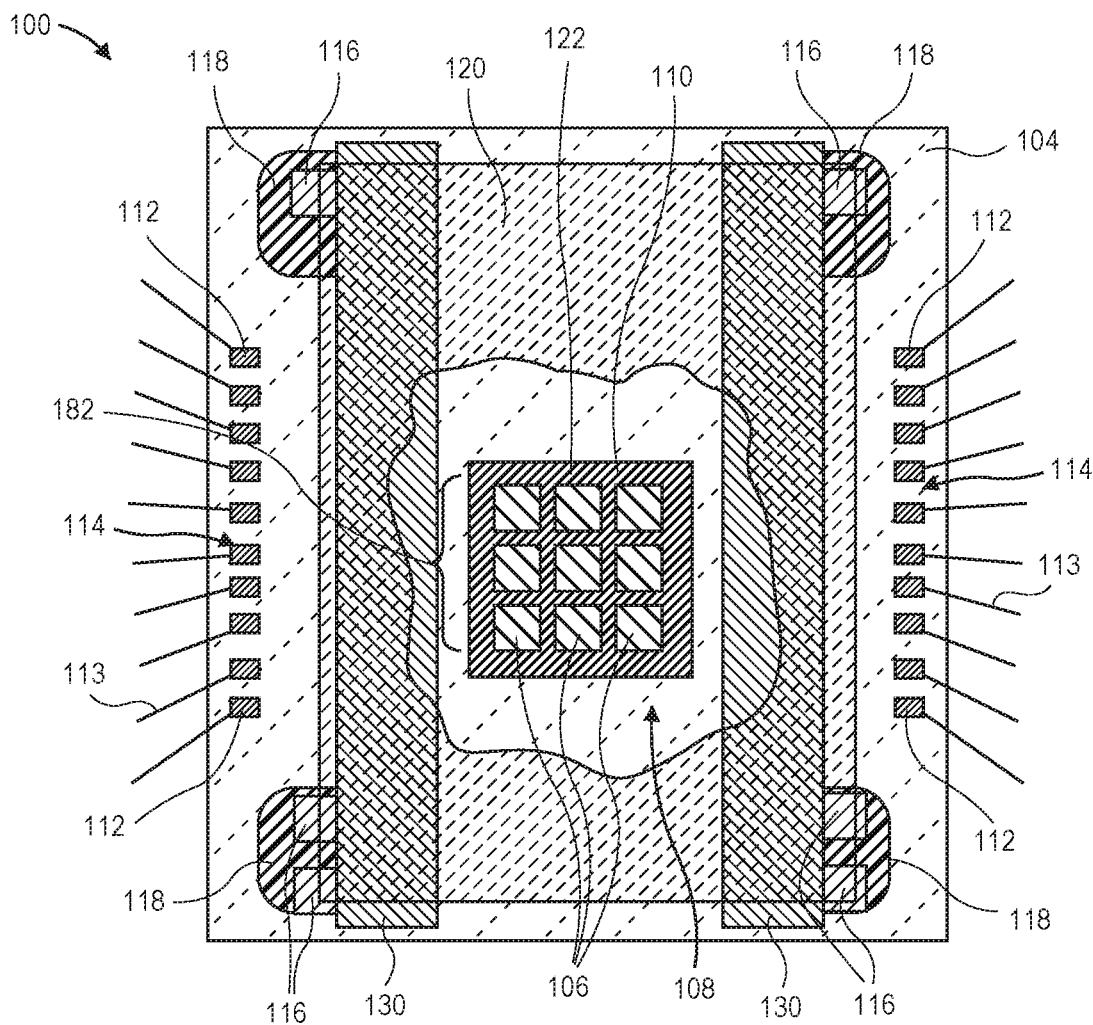
FIG. 1C is a partial top plan view illustrating an embodiment of a sensor chip and sensor package having an array of conductive elements with dispense chemistry disposed on the array of conductive elements and including spacers, in accordance with an example implementation of the present disclosure.
Figure 1D:
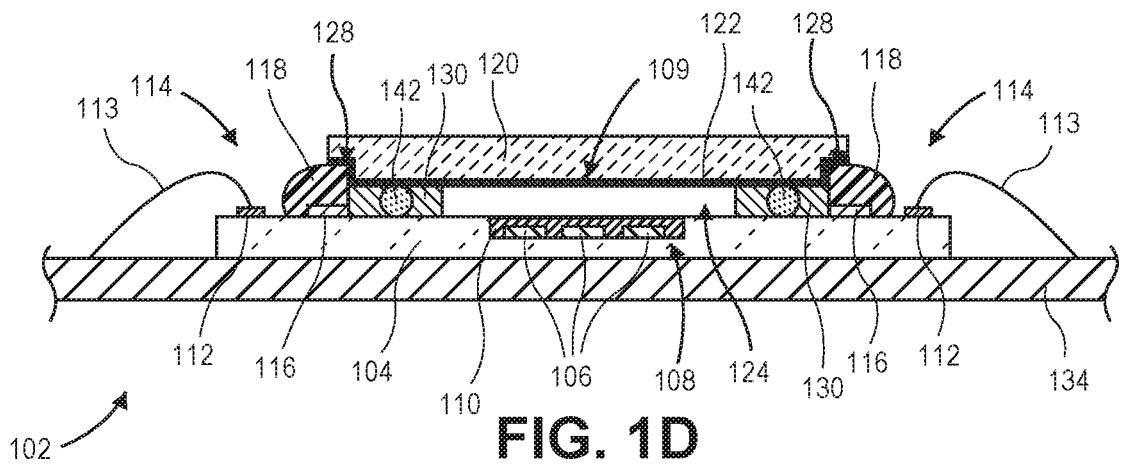
FIG. 1D is a cross-sectional side view illustrating an embodiment of a sensor chip and sensor package having an array of conductive elements with dispense chemistry disposed on the array of conductive elements and including spacers, in accordance with an example implementation of the present disclosure.

Referring now to FIGS. 1A through 1F, the at least one bonding pad 112 may be disposed on the sensing chip 104 proximate to the periphery 114 of the sensing chip 104. The at least one bonding pad 112 may be configured to provide a bonding surface and an electrical connection between the sensing chip 104 and a printed circuit board (not shown) or to another component of the sensor package 102. For example, at least one wire bond 113 can be coupled to the at least one bonding pad 112, respectively. As illustrated in FIGS. 1B and 1D, multiple wire bonds 113 may couple a plurality of bonding pads 112 to a base substrate 134 (e.g., a printed circuit board and/or flexible, printed plastic). It is contemplated that the at least one bonding pad 112 can be configured to be coupled to another electrical component in a variety of other ways, such as, for example, using solder bumps or other such connections.

Referring now to FIGS. 1A through 1I, in an example implementation of the disclosure, the sensing chip 104 may include dispense chemistry 110 disposed on the array of conductive elements 106. The dispense chemistry 110 can be disposed on and/or may cover the conductive panel(s) 106 and/or within the top via 170 (FIGS. 1H and 1I), the exposed side 176 (FIGS. 1H and 1I), the passivation via 172 (FIGS. 1H and 1I), and/or the exposed side 178 (FIGS. 1H and 1I) such that the surface of the sensing chip 104 and/or the top dielectric layer 180 (FIG. 1I) may be substantially planar. In one embodiment, the dispense chemistry 110 may be disposed on the array of conductive elements 106 including the space in between each respective conductive element 106. In another embodiment, the dispense chemistry 110 may be disposed on at least one conductive element 106 in the array of conductive elements 106 with no dispense chemistry 110 disposed on the space between at least two conductive elements 106. The dispense chemistry 110 can include, for example, a water-based polymer solution/particle mixture that can be dried on the sensing chip 104. In one embodiment, the dispense chemistry 110 can include a total solid content of approximately 5% v/v with a particle content of approximately 0.5% and a particle size of approximately 0.4-3 µm. In an example embodiment of the disclosure, the dispense chemistry 110 may be in the form of a film disposed over the at least one conductive element 106, where the thickness of the dispense chemistry 110 may be approximately 1 µm. The dispense chemistry 110 can include a variety of biomaterials to perform a variety of assays. An assay may include a test performed by adding one or more reagents to a sample (e.g., a fluid sample that enters cavity 124, for example by capillary action) for testing by the sensing chip 104 and the sensor package 102) and analyzing how the sample or the reagents may be consequently affected. For example, functionalized beads (e.g., beads comprising or coated with one or more reagents) may agglutinate or agglomerate when a certain analyte may be present in the fluid sample. Some examples of assays may be agglutination or agglomeration assays including, but not limited to, immunoassays, kinetic agglutination assays, agglomeration-of-beads assays, kinetic agglomeration-of-beads assays, coagulation assays, kinetic coagulation assays, surface antigen assays, receptor assays from biopsy procedures, circulating blood cells assays, circulating nucleic acid assays, and so on. It is contemplated that the dispense chemistry 110 may include other configurations, solid content, particle content, thickness, particle size, and may be configured for other assays. For example, the dispense chemistry 110 may be disposed on a side of the microfluidic cap 120 proximate to at least one conductive element 106.

As illustrated in FIGS. 1A through 1D, the sensor package 100 may include the microfluidic cap 120 disposed over a portion of the sensing chip 104. In embodiments, the microfluidic cap 120 can include glass (e.g., a glass plate), a polymer, ceramic, a creaming, and/or other electrically non-conductive and/or dielectric materials. Additionally, the microfluidic cap 120 may be disposed over the array of conductive elements 106, where a surface of the microfluidic cap 120 proximate to the sensing chip 104 may be substantially planar and parallel with the surface of the sensing chip 104 and/or the top dielectric layer 180 of the sensing chip 104. The microfluidic cap 120 and the sensing chip 104 may define a cavity, such as the cavity 124 of FIG. 1B. In the embodiment shown in FIGS. 1A and 1B, the microfluidic cap 120 can include a central etched gap 126 that may be configured to control cavity spacing between the microfluidic cap 120 and the sending chip 104. The microfluidic cap may include at least one etched edge gap 128 that may be configured to allow the at least one conductive adhesive 118 to be formed between the microfluidic ca 120 and the sensing chip 104. The central etched gap 126 can be disposed on and/or proximate to a central portion 109 of a cross section of the microfluidic cap 120 and proximate to the sensing chip 104. The central etched gap 126, the sensing chip 104, and the microfluidic cap 120 may also define the cavity 124 that may be configured for at least partially containing a liquid or fluid sample for analysis by the array of conductive plates 106 and the sensing chip 104. Additionally, the microfluidic cap 120 may include at least one etched edge gap 128 disposed along at least one edge of the microfluidic cap 120 and proximate to the sensing chip 104. The at least one etched edge gap 128 can be configured to partially contain, facilitate, and/or allow the adhesive 118. The adhesive 118 can contact the sensing chip 104 and the etched edge gap 128, and when a conductive adhesive 118 is utilized, the conductive adhesive 118 can provide an electrical connection between a contact pad 116 on the sensing chip 104 and the microfluidic cap 120 (e.g., electrical contact between the conductive adhesive 118 and the electrode 122 on the microfluidic cap 120). Furthermore, at least one structure may be formed on and/or within the microfluidic cap 120, such as a bluff and/or a mesa.

In the example embodiments illustrated in FIGS. 1C and 1D, a spacer 130 may be disposed on the sensing chip 104 and/or the top dielectric layer 180, and the microfluidic cap 120 can be disposed on the spacer 130. The microfluidic cap 120, in this embodiment, may not include a central etched gap 126, but may depend on the spacer 130 to provide a standoff height between the microfluidic cap 1200 and the sensing chip 104. In this embodiment, the microfluidic cap 120, the at least one spacer 130, and the sensing chip 104 can at least partially define the cavity 124. In implementations, the spacer 130 can include, for example, at least one bead 142 and/or a rod (e.g., where the rod may extend at least a partial length of the microfluidic cap 120). The bead 142 and/or the rod can provide mechanical support for the spacer 130 and/or the microfluidic cap 120.

Referring now to FIGS. 1A through 1D, the sensor package 102 can include at least one electrode 122 disposed on and/or embedded within the microfluidic cap 120 (e.g., on and/or within a surface of the microfluidic cap 120 that may be proximate to and/or facing the sensing chip 104). The at least one electrode 122 may be flat on the microfluidic cap 120 and/or may include multiple surfaces having different distances from the sensing chip 104 and/or at least one of the conductive elements 106, where the multiple surfaces may allow for different sensitivities and/or can be used to filter a liquid sample such that each portion of the sensor area below the multi-level electrode may be sensitive to a different range of particle sizes. The electrode 122 may be electrically coupled to the sensing chip 104 using, for example, a conductive adhesive 118. Some examples of an electrode 122 may include a working electrode, a reference electrode, and/or an auxiliary or counter electrode, such as for an electrochemical cell. In one example embodiment of the disclosure, the electrode 122 can include a partitioned counter electrode disposed on the microfluidic cap 120. In this embodiment, the partitioned electrode can include an electrode that may be formed on different portions of the microfluidic cap 120 and can be at least partially separated by space on the microfluidic cap 120 that may not be covered by the electrode 122. In another example embodiment, the at least one electrode 122 may include one or more partitions that may be configured to create a plurality of potential zones that may be configured to isolate one or more assays. The electrode 122 can be configured to transmit at least one electrical signal through a fluid sample to the at least one conductive panel 106, and the at least one conductive panel 106 can be configured to generate a sense signal at least partially based on the signal (e.g., electrical signal) transmitted by the electrode 122, where the electrode 122 and/or the at least one conductive panel 106 can be electrically and/or communicatively coupled to the sensing chip 104 and/or a controller. A sense signal can be affected by impedance or capacitance between the electrode 122 and a respective conductive panel 106 resulting from one or more particles in the fluid sample. For example, a conductive panel 106 positioned below a portion of the fluid sample having a first concentration of particles or a first sized particle may produce a different (e.g., more or less powerful) sense signal than another conductive panel 106 positioned below a portion of the fluid sample having a second (different) concentration of particles, no particles, or a second (different) sized particle as a result of differing impedance or capacitance characteristics of the respective portion of the fluid sample.

In some implementations, an encapsulation layer 132 may be at least partially disposed on/over the at least one wire bond 113, bonding pad 112, adhesive 118, and/or the sensing chip 104. For example, FIGS. 1A and 1B illustrate an encapsulation layer 132 disposed over the wire bonds 113 for protecting the adhesive 118, the bonding pad 112, the wire bonds 113, and/or parts of the sensing chip 104 from environmental factors. Some examples of materials suitable for an encapsulation layer 132 can include an epoxy and/or a polymer. It is contemplated that the encapsulation layer 132 may include a variety of other materials and/or configurations.

As shown in FIGS. 1B and 1D, a sensor system 102 may include a sensing chip 104 and/or a sensor package 100 coupled to a base substrate 134 (e.g., a printed circuit board and/or flexible, printed plastic). In embodiments, the sensing chip 104 can be mechanically and/or electrically coupled using, for example, at least one solder connection and/or an adhesive (e.g., a die attach adhesive). The sensor system 102 may be configured to be included within, embedded to, and/or coupled to another device, such as a mobile device (e.g., a smartphone, wearable device, tablet, digital camera, notebook computer, media player, portable gaming device, or the like), a computer, an analysis instrument, or the like.

Figure 1E:
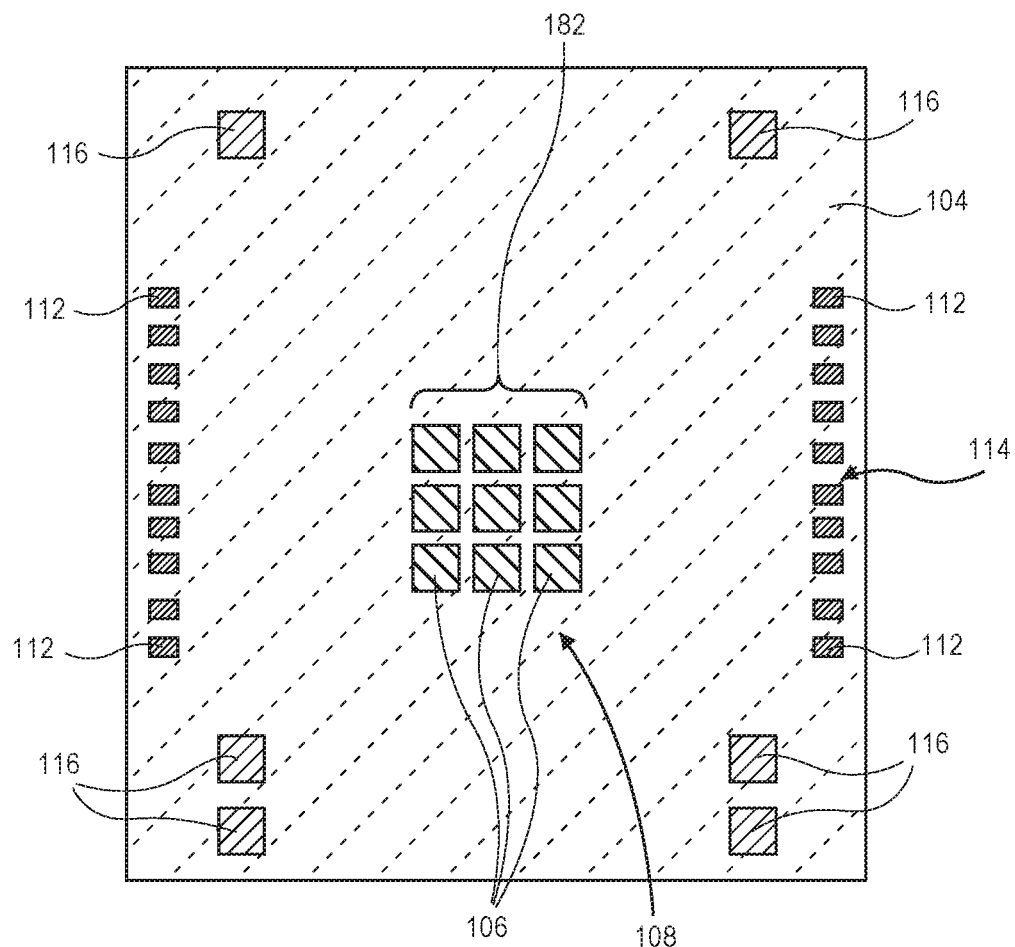
FIG. 1E is a top plan view illustrating an embodiment of a sensor chip having an array of conductive elements with dispense chemistry disposed on the array of conductive elements, in accordance with an example implementation of the present disclosure.
Figure 1F:
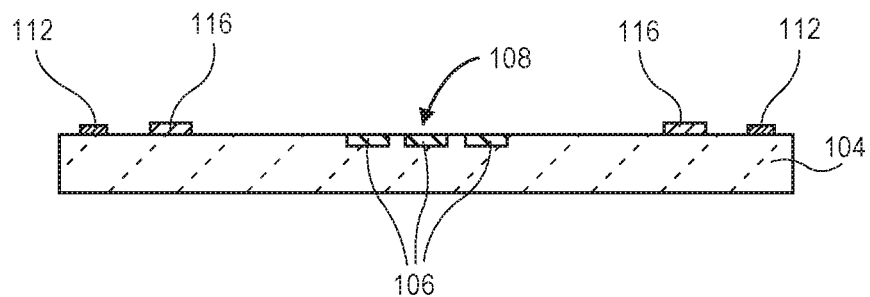
FIG. 1F is a cross-sectional side view illustrating an embodiment of a sensor chip having an array of conductive elements with dispense chemistry disposed on the array of conductive elements, in accordance with an example implementation of the present disclosure.

Referring now to FIGS. 1E and 1F, illustrated respectively are top plan view and cross-sectional side view of an example sensor chip 104 that may include an array of conductive elements 106. It may be appreciated that the upper most layer of the sensor chip 104 including the upper inter layer dielectric (not shown) may be substantially planar. The surfaces that may be covered by the top electrode 122 in the microfluidic cap 120 and those in the region between adjacent arrays 106 may also be substantially planar so that any analyte may flow evenly and cover the arrays 106. Gaps between arrays 106 as well as the upper most layer of the sensor chip 104 and the upper (cap electrode) surface of the microfluidic cap 120 may also be substantially planar.

Figure 1G:
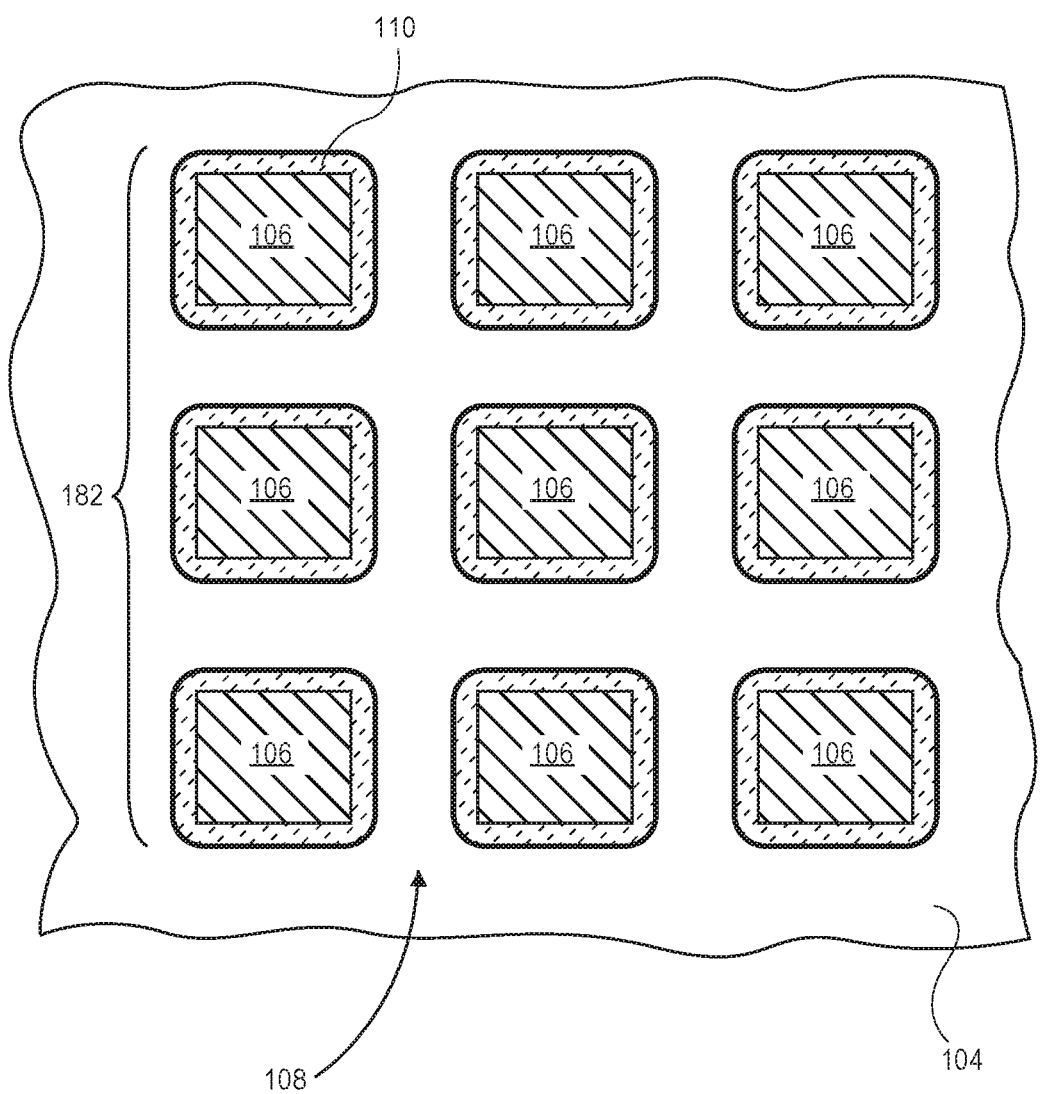
FIG. 1G is a top plan view illustrating an embodiment of one or more arrays of conductive elements on a sensor chip with targeted chemistry island after dispensing and drying, in accordance with an example implementation of the present disclosure.

Referring now to FIG. 1G, a top plan view of an example sensor chip 104 is illustrated. Indicated are arrays of conductive elements 106 that may be located proximate to the center 108 of the sensor chip 104. As indicated in FIG. 1G, dispense chemistry 110 may cover each individual array of conductive elements 106 with space in between with no dispense chemistry. Dispense chemistry 110 covering each array of conductive elements 106 may be considered as targeted chemistry island. Targeted chemistry islands may result after dispensing and drying of the dispense chemistry 110. In an example embodiment of the disclosure, there may be defined minimum and maximum separation distances between chemistry islands. For example, the minimum separation distance between chemistry islands may be of the order of 50 µm, 100 µm, 150 µm, 200 µm, 500 µm and so on. Also, there may be defined minimum and maximum overlap of array of conductive elements 106 with dispense chemistry 110. For example, the overlap of array of conductive elements 106 with dispense chemistry 110 may be at 0 µm in some case, or it may be 10 µm, 20 µm, 40 µm, 56 µm, 100 µm, and so on.

Figure 1H:
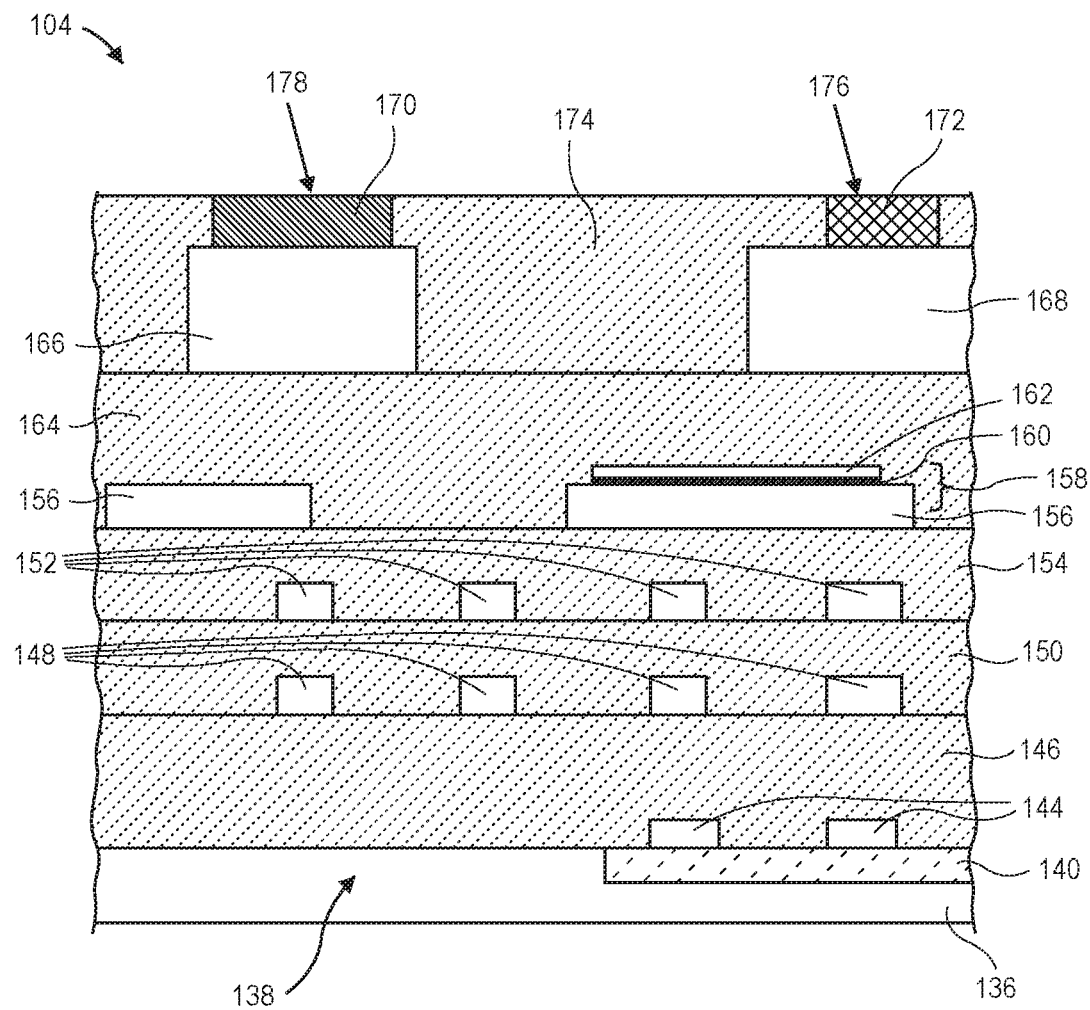
FIG. 1H is a cross section side view illustrating an architecture of a sensor chip having an array of conductive elements, in accordance with an example implementation of the present disclosure.

In the embodiment illustrated in FIG. 1H, the sensing chip 104 shown includes a substrate 136 having an active portion 138. The substrate 136 can include a variety of materials and/or configurations, such as a semiconductor material (e.g., silicon), a shallow trench isolation oxide 140 (and/or a field oxide (FOX)), and/or the active portion 138 that has been processed to include active circuitry. For example, the substrate 136 and/or the active portion 138 may comprise an n-type silicon wafer or a p-type silicon wafer. In an implementation, the substrate 136 and/or the active portion 138 may comprise group V elements (e.g., phosphorus, arsenic, antimony, etc.) configured to furnish n-type charge carrier elements. In another implementation, the substrate 136 and/or the active portion 138 may comprise group IIIA elements (e.g., boron, etc.) configured to furnish p-type charge carrier elements. Further, the substrate 136 and/or the active portion 138 can include integrated circuits, which may be configured in a variety of ways. For example, the integrated circuits may include digital integrated circuits, analog integrated circuits, mixed-signal circuits, and so forth. In one or more implementations, the integrated circuits may include digital logic devices, analog devices (e.g., amplifiers, etc.), combinations thereof, and so forth. As described above, the integrated circuits may be fabricated utilizing various fabrication techniques. For example, the integrated circuits may be fabricated via complimentary metal-oxide-semiconductor (CMOS) techniques, bi-polar semiconductor techniques, and so forth.

Continuing with the embodiment illustrated in FIG. 1H, the sensing chip 104 can include a base conductive layer 144 disposed on the substrate 136 and on the shallow trench isolation oxide 140 (and/or a field oxide (FOX), which may replace and/or be in addition to the shallow trench oxide 140). A first interlayer dielectric 146 can be disposed on and/or surrounding the base conductive layer 144, the shallow trench isolation oxide 140, and/or the substrate 136. A series of conductive layers and interlayer dielectrics may be disposed on the first interlayer dielectric 146, which can include a first conductive layer 148 that may be disposed on the first interlayer dielectric 146, a second interlayer dielectric 150 that may be disposed on and/or surrounding the first conductive layer 148, a second conductive layer 152 that may be disposed on the second interlayer dielectric 150, a third interlayer dielectric 154 that may be disposed on and/or around the second conductive layer 152, a third conductive layer 156 that may be disposed on the third interlayer dielectric 154, a fourth interlayer dielectric 164 that may be disposed on and/or around the third conductive layer 156, and a first top conductive layer 166 and second top conductive layer 168 that may be disposed on the fourth interlayer dielectric 164. Additionally, a top via 170 can be disposed in the fourth interlayer dielectric 164 and over the first top conductive layer 166, and a passivation via or passivation layer 172 can be disposed in the fourth interlayer dielectric 164 and over the second top conductive layer 168. In implementations, the first top conductive layer 166 and/or the second top conductive layer 168 can include and/or be configured as at least one conductive panel 106 disposed on a surface of the sensing chip 104. Additionally, the first top conductive layer 166, the second top conductive layer 168, and/or the at least one conductive element 106 may be disposed proximate to a center 108 of the sensing chip 104. It is contemplated that the embodiments illustrated in FIG. 1H and FIG. 1I may also be implemented without passivation vias or passivation layers.

Figure 1I:
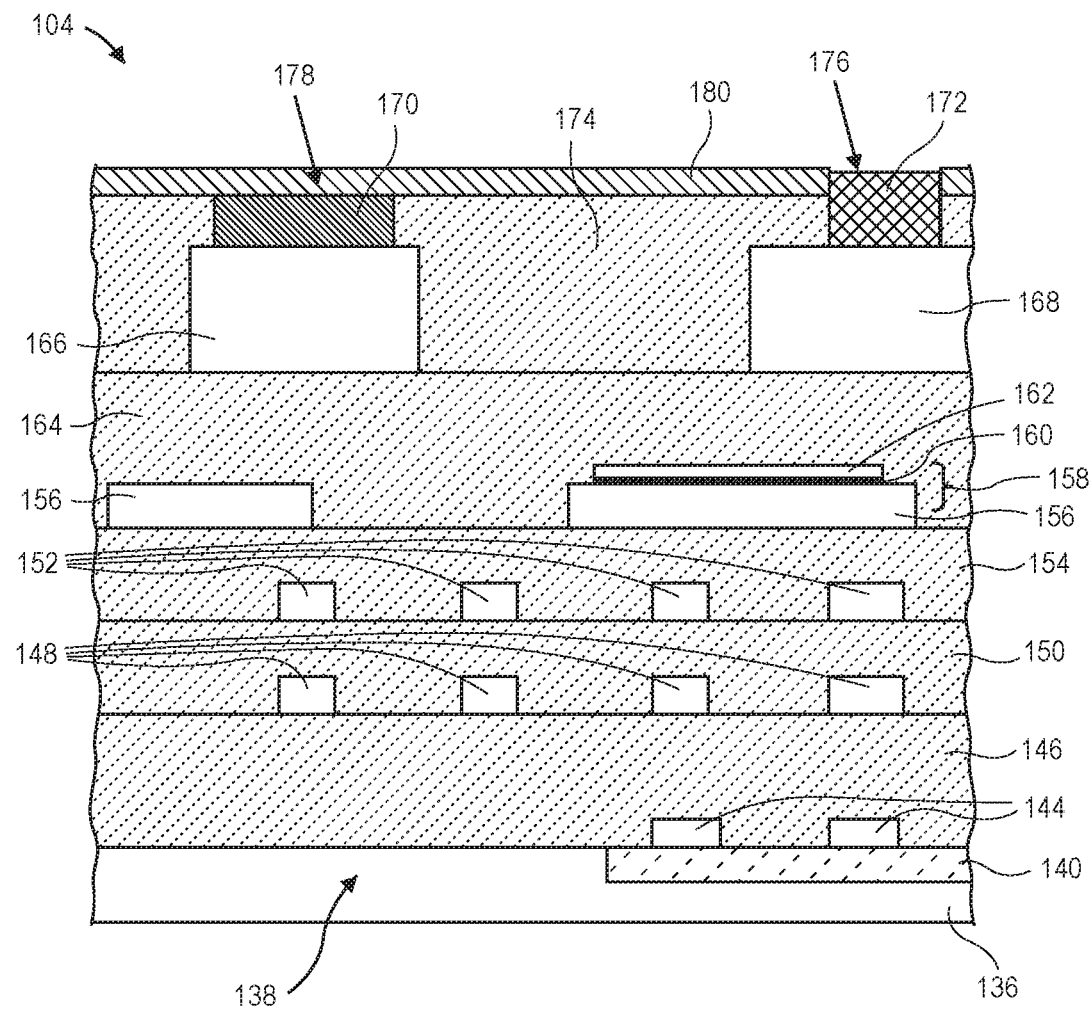
FIG. 1I is a cross section side view illustrating an architecture of a sensor chip having an array of conductive elements and including a top dielectric layer, in accordance with an example implementation of the present disclosure.

The embodiment illustrated in FIG. 1I shows a sensing chip 104 that may include a base conductive layer 144 that may be disposed on the substrate 136 and on the shallow trench isolation oxide 140. A first interlayer dielectric 146 can be disposed on and/or surrounding the base conductive layer 144, the shallow trench isolation oxide 140, and/or the substrate 136. A series of conductive layers and interlayer dielectrics may be disposed on the first interlayer dielectric 146, which can include a first conductive layer 148 that may be disposed on the first interlayer dielectric 146, a second interlayer dielectric 150 that may be disposed on and/or surrounding the first conductive layer 148, a second conductive layer 152 that may be disposed on the second interlayer dielectric 150, a third interlayer dielectric 154 that may be disposed on and/or around the second conductive layer 152, a third conductive layer 156 that may be disposed on the third interlayer dielectric 154, a fourth interlayer dielectric 164 that may be disposed on and/or around the third conductive layer 156, and a first top conductive layer 166 and second top conductive layer 168 that may be disposed on the fourth interlayer dielectric 164. Additionally, a top via 170 can be disposed in the fourth interlayer dielectric 164 and over the first top conductive layer 166, and a passivation via 172 can be disposed in the fourth interlayer dielectric 164 and over the second top conductive layer 168.

Again referring to the example embodiment illustrated in FIG. 1I, a top dielectric layer 180 can be disposed on and/or over the fifth interlayer dielectric 174 and/or the top via 170. In this embodiment, at least one via (e.g., the passivation via 172) can extend through the top dielectric layer 180 and leave the first top conductive layer 166 and/or the second top conductive layer 168 exposed from the sensing chip 104 (e.g., exposed side 176 of the passivation via 172, exposed side 178 of the top via 170). In the embodiment illustrated in FIG. 1I, the second top conductive layer 168 can include and/or be configured as at least one conductive panel 106 disposed on a surface of the sensing chip 104. Additionally, the fifth interlayer dielectric 174 and/or the top dielectric layer 180 can be planarized to provide a substantially smooth surface of the sensing chip 104. Planarity of the fifth dielectric interlayer dielectric 174, the top via 170, the passivation via 172, and/or the sensing chip 104 may be important for integration of the electrode(s) 122 and entry of a fluid sample into cavity 124. For example, the electrode 122 (e.g., excitation electrode) can be coplanar with the sensing chip 104 and the conductive element 106 (e.g., the sensing array). It is also contemplated that more or less layers of interlayer dielectrics and/or conductive layers (e.g., metal layers) may be utilized within the sensing chip 104.

In the embodiments illustrated in FIGS. 1H and 1I, the sensing chip 104 may include a metal-insulator-metal capacitor 158 that may be configured to provide a capacitance reference value by the sensing chip 104, the active portion 138, and/or other active circuitry within the sensor package 102. In the specific embodiments shown in FIGS. 1H and 1I, the metal-insulator-metal capacitor 158 may be disposed on the third interlayer dielectric 154. However, the metal-insulator-metal capacitor 158 may be disposed on any interlayer dielectric within the sensing chip 104. In an implementation, the metal-insulator-metal capacitor 158 can include a third conductive layer 156 disposed on the third interlayer dielectric 154, a dielectric layer 160 disposed on the third conductive layer 156, and a capacitance conductive layer 162 that may be disposed on the dielectric layer 160, where the fourth interlayer dielectric 164 can be substantially disposed on and/or surrounding the metal-insulator-metal capacitor 158. It is contemplated that the sensing chip 104 can include other components, such as additional transistors, circuits, capacitors, diodes, and so forth.

Example Processes

Figure 2:
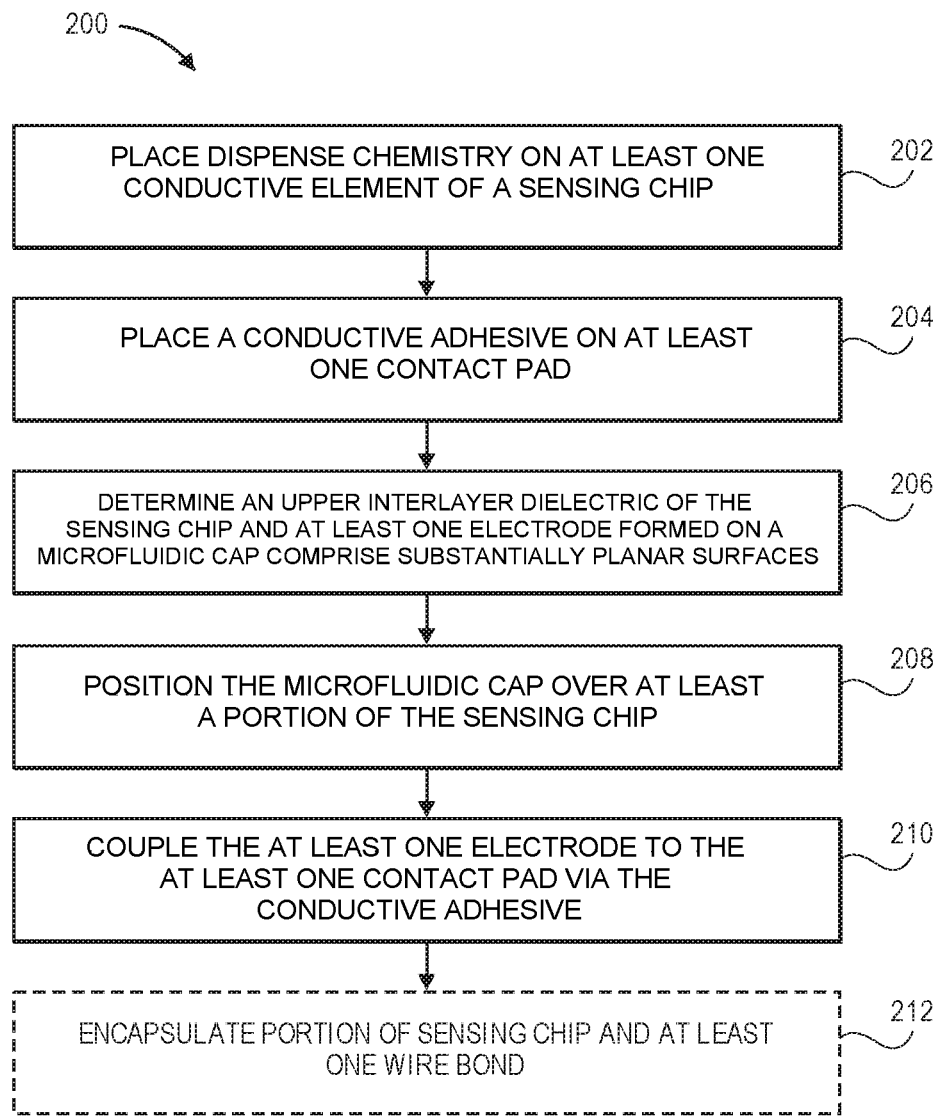
FIG. 2 is a flow diagram illustrating an example process for fabricating a sensor chip and sensor package having an array of conductive elements with dispense chemistry disposed on the array of conductive elements, such as the sensor chip and sensor package illustrated in FIGS. 1A through 1I.
Figure 3A:
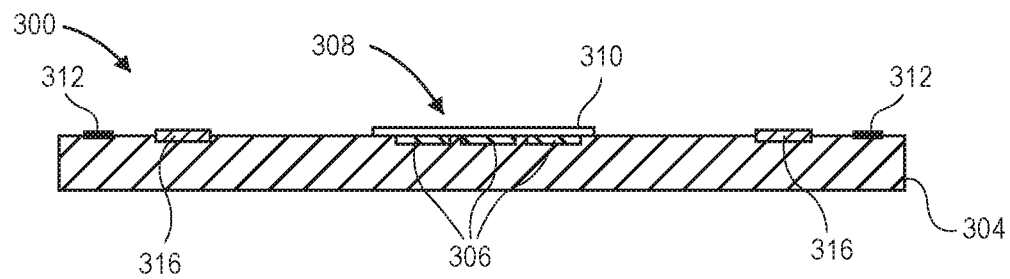
FIG. 3A is a cross section side view illustrating the fabrication of a sensor chip and sensor package having an array of conductive elements with dispense chemistry disposed on the array of conductive elements, such as the sensor chip and sensor package shown in FIGS. 1A through 1I, in accordance with the process shown in FIG. 2.
Figure 3B:
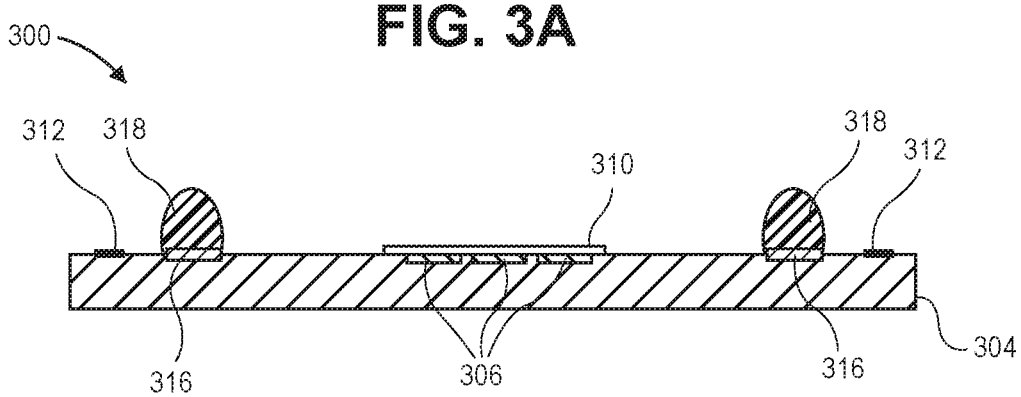
FIG. 3B is a cross section side view illustrating the fabrication of a sensor chip and sensor package having an array of conductive elements with dispense chemistry disposed on the array of conductive elements, such as the sensor chip and sensor package shown in FIGS. 1A through 1I, in accordance with the process shown in FIG. 2.
Figure 3C:
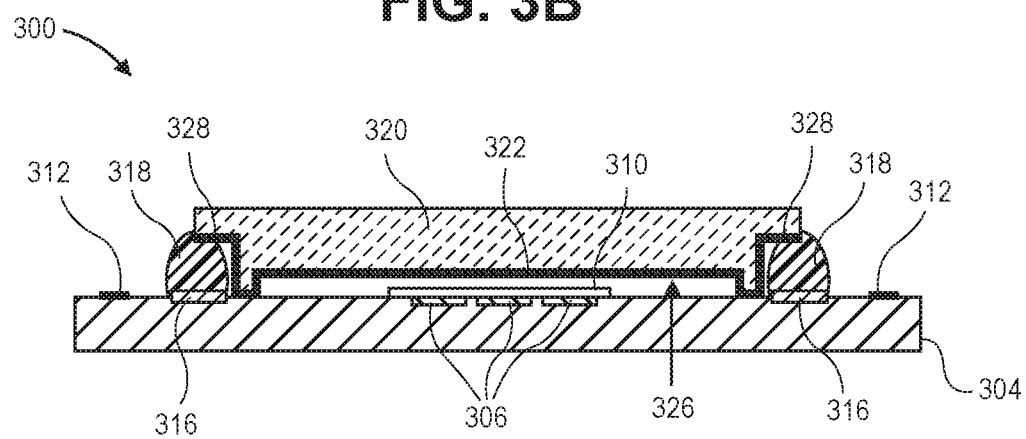
FIG. 3C is a cross section side view illustrating the fabrication of a sensor chip and sensor package having an array of conductive elements with dispense chemistry disposed on the array of conductive elements, such as the sensor chip and sensor package shown in FIGS. 1A through 1I, in accordance with the process shown in FIG. 2.
Figure 3D:
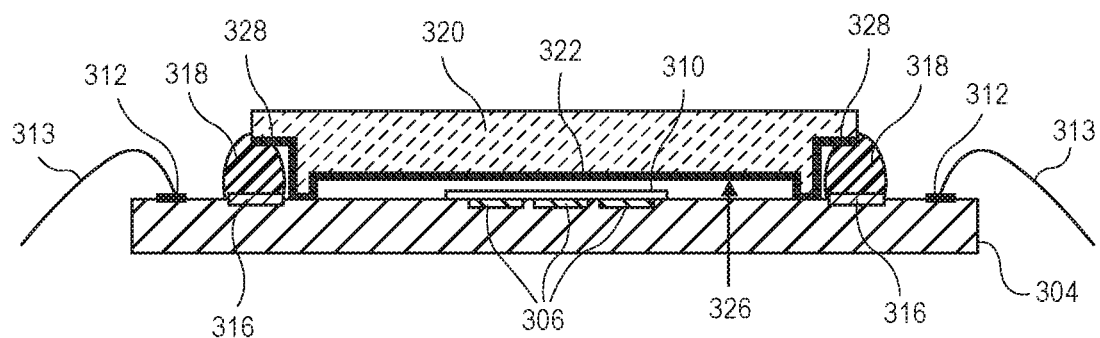
FIG. 3D is a cross section side view illustrating the fabrication of a sensor chip and sensor package having an array of conductive elements with dispense chemistry disposed on the array of conductive elements, such as the sensor chip and sensor package shown in FIGS. 1A through 1I, in accordance with the process shown in FIG. 2.
Figure 3E:
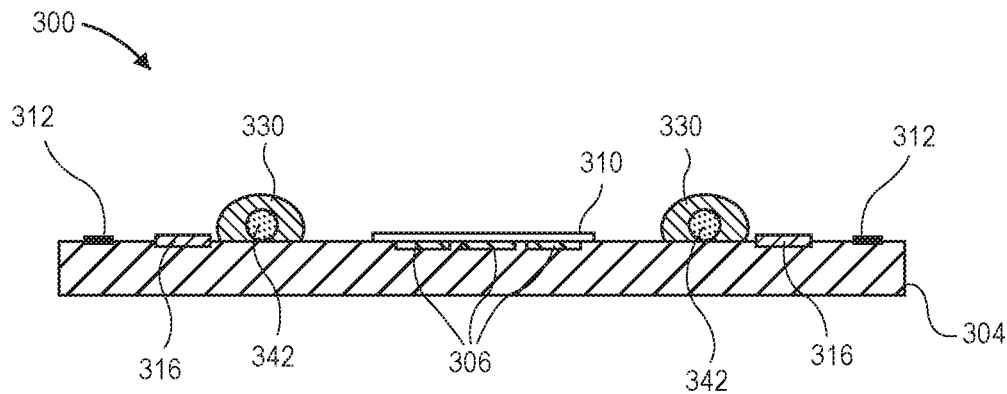
FIG. 3E is a cross section side view illustrating the fabrication of a sensor chip and sensor package having an array of conductive elements with dispense chemistry disposed on the array of conductive elements, such as the sensor chip and sensor package shown in FIGS. 1A through 1I, in accordance with the process shown in FIG. 2.
Figure 3F:
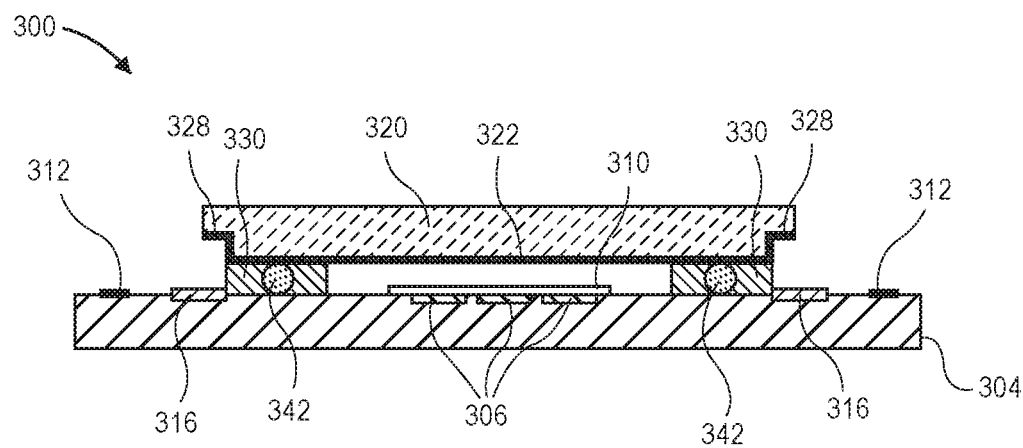
FIG. 3F is a cross section side view illustrating the fabrication of a sensor chip and sensor package having an array of conductive elements with dispense chemistry disposed on the array of conductive elements, such as the sensor chip and sensor package shown in FIGS. 1A through 1I, in accordance with the process shown in FIG. 2.
Figure 3G:
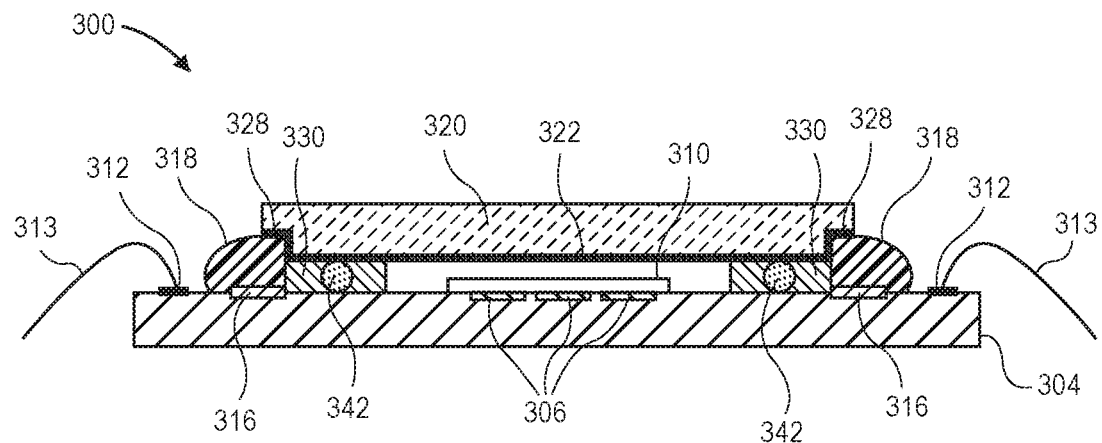
FIG. 3G is a cross section side view illustrating the fabrication of a sensor chip and sensor package having an array of conductive elements with dispense chemistry disposed on the array of conductive elements, such as the sensor chip and sensor package shown in FIGS. 1A through 1I, in accordance with the process shown in FIG. 2.

FIG. 2 illustrates an example process 200 that employs techniques to fabricate a sensing chip, a sensor package, and a sensing system, such as the sensing chip 104, the sensor package 100, and the sensing system 102 shown in FIGS. 1A through 1I. FIGS. 3A through 3G illustrate a section of a sensing chip during fabrication (such as the sensing chip 104 shown in FIGS. 1A through 1I). In general, operations of disclosed processes (e.g., process 200) may be performed in an arbitrary order, unless otherwise provided in the claims.

In the process 200 illustrated, dispense chemistry may be placed 202 on at least one conductive element of a sensing chip. In an example embodiment, the at least one conductive element may be part of an array of conductive elements that may define a M by N matrix, where M is a number of rows of the at least one conductive element and N is a number of columns of the at least one conductive element, and wherein the sensing chip may further include at least one contact pad. In the implementation illustrated in FIG. 3A, a sensing chip 304 can be received, where the sensing chip 304 may include an array of at least one conductive element 306 that may be disposed proximate to a center 308 of the sensing chip 304, at least one bonding pad 112, and at least one contact pad 116. Then, dispense chemistry 310 may be placed on and/or formed on the at least one conductive element 306, the exposed side 176, the exposed side 178, and/or a surface of the sensing chip 304 (e.g., the top dielectric layer 180). In an example implementation, placing the dispense chemistry 310 on the conductive element(s) 306 and/or the sensing chip 304 can include spraying, dropping, and/or otherwise applying a liquid dispense chemistry 310 onto the conductive element(s) 306 and/or the sensing chip 304. In an example implementation, placing the dispense chemistry 310 on the conductive element(s) 306 and/or the sensing chip 304 can include preforming the dispense chemistry 310 and subsequently placing the dispense chemistry 310 on the conductive element(s) 306 using a pick-and-place type process and equipment. It is contemplated that other methods for placing the dispense chemistry 310 may be utilized. Additionally, the dispense chemistry 310 may be dried or allowed to dry, for example, using air convection and/or heat. As illustrated in FIG. 1G, the dispense chemistry after drying may form chemistry islands. In some implementations, the dispense chemistry 310 may be dried using a drying enhancer that can be added to the liquid dispense chemistry 310, such as a maltodextrin, a detergent, and/or an alcohol. In an embodiment, placing the dispense chemistry 310 on the conductive element(s) 306 and/or the sensing chip 304 can include placing the dispense chemistry 310 over the entire array of conductive element(s) 306 including the area of the sensing chip 304 disposed between each respective conductive element 306. In an embodiment, placing the dispense chemistry 310 on the conductive element(s) 306 and/or the sensing chip 304 can include placing the dispense chemistry 310 only on each respective conductive element 306 in the array and not on the area of the sensing chip 304 disposed between each respective conductive element 306. Although the dispense chemistry 310 may be illustrated in the figures as non-planar with the surface of the sensing chip 304 (for illustration purposes), the dispense chemistry 310 can placed such that the dispense chemistry 310 may be planar or substantially planar with the surface of the sensing chip 304.

Referring again to the process diagram of FIG. 2, the process 200 may further include placing 204 a conductive adhesive on at least one contact pad, wherein the contact pad may be disposed on the sensing chip. In the implementation illustrated in FIG. 3B, a conductive adhesive 318 may be placed on at least one contact pad 316 on the sensing chip 304. In this implementation, placing the conductive adhesive 318 can include using a spraying, dropping, and/or brushing process to apply the adhesive 318, which may be liquid. In an embodiment, placing the conductive adhesive 318 can include placing a conductive epoxy. In some implementations, such as the implementation illustrated in FIG. 3G, placing an adhesive 318 can occur subsequent to placing a microfluidic cap 320.

In some implementations, a spacer 330 and/or a bead 342 may be placed on the sensing chip 304. Placing the spacer 330 and/or a bead 342 may include placing and/or dispensing the spacer 330 and/or bead 342 as a liquid, a partial liquid, and/or as a solid on the sensing chip 304. Additionally, placing the spacer 330 may include adding at least one bead 342 and/or rod to the spacer 330 to provide mechanical support to the spacer 330 and/or a microfluidic cap 320.

In an example implementation of the disclosure, the method 200 may further include determining 206 an upper interlayer dieelectric of the sensing chip and at least one electrode formed on a microfluidic cap comprise substantially planar surfaces. This may be done to ensure that, in the final assembly, a cavity formed between the sensing chip and the microfluidic cap may facilitate even distribution and flow of analyte or test sample fluid.

As illustrated in FIGS. 3C-3D, and 3F-3G, the process 200 may further include an intermediate step of forming at least one electrode on the microfluidic cap. In an embodiment, forming the at least one electrode 322 on the microfluidic cap 320 can include forming one electrode 322 proximate to an array of conductive elements 306. In this embodiment, the electrode 322 may or may not be formed as a partitioned electrode 322 (e.g., the electrode 322 can be formed on only some parts of the microfluidic cap 320, a first portion of the electrode 322 may be separated by space from a second portion of the same electrode 322). In an embodiment, forming the at least one electrode 322 can include forming two (or more) electrodes 322, where one electrode 322 may be formed on the microfluidic cap 320 proximate to a first set of metal panel(s) 306, and a second electrode 322 may be formed in the microfluidic cap 320 proximate to a second set of metal panel(s) 306. In this embodiment, the first electrode 322 and the second electrode 322 may be electrically coupled to the same or different portions of the adhesive 318 and/or the sensing chip 304. In some implementations, forming the at least one electrode 322 on the microfluidic cap 320 can include using a pick-and-place process to place the electrode(s) 322, which can include a conductive material, such as a metal. In some implementations, forming the at least one electrode 322 can include depositing the electrode(s) 322 using a plating technique, a spraying technique (e.g., spraying a conductive ink). In some implementations, forming the at least one electrode 322 on the microfluidic cap 320 may include using a photolithographic process, such as deposition (e.g., physical vapor deposition, chemical vapor deposition, sputtering, and so forth), masking, and/or etching. It is contemplated that other processes may be utilized for forming the at least one electrode 322 on the microfluidic cap 320.

The process 200 may further include positioning 208 a microfluidic cap on the adhesive and a portion of the sensing chip. In implementations, positioning 208 a microfluidic cap 320 on the adhesive 318 can include using a pick-and-place operation to place the adhesive 318. In the implementation illustrated in FIG. 3C, the microfluidic cap 320 can include an etched edge gap 328, which can be configured to allow the adhesive 318 to flow and adhere to microfluidic cap 320. Additionally, a portion of the microfluidic cap 320 can abut the sensing chip 304, and a central etched gap 326, which can be formed in the microfluidic cap 320, can be placed proximate to and over the array of metal plate(s) 306. In the example implementation illustrated in FIGS. 3F and 3G, the microfluidic cap 320 can be placed on the spacer 330 prior to placing the adhesive 318 on the at least one contact pad 316. In this implementation, the adhesive 318 can be placed abutting and/or within the etched edge gap 328, the microfluidic cap 320, the spacer 330, the at least one contact pad 316, and/or the sensing chip 304. The microfluidic cap 320 can be placed substantially planar with and parallel to the sensing chip 304 and the array of metal panel(s) 306. In implementations, placing the microfluidic cap 320 on the adhesive 318 and/or the sensing chip 304 can include coupling an electrode 322 on and/or embedded in the microfluidic cap 320 to a conductive adhesive 318.

Referring again to the process 200 of FIG. 2, the at least one electrode of the microfluidic cap may be coupled 210 to the at least one contact pd via the conductive adhesive. In an example embodiment, at least one wire bond may be placed 210 on at least one bonding pad disposed proximate to the periphery of the sensing chip. In implementations, placing at least one wire bond 313 can include using a bonding process, such as ball bonding and/or compliant bonding. Placing the at least one wire bond 313 can include coupling the at least one wire bond 313 to a bonding pad 312 disposed on the sensing chip 304 and/or a bonding pad disposed on another electrical component, such as a base substrate 134 (e.g., a printed circuit board and/or flexible, printed plastic)).

In an example implementation, at least a portion of the sensing chip and at least one wire bond may be encapsulated 212 with an encapsulation layer. Encapsulating 212 at least one wire bond 313 and/or a portion of the sensing chip 304 may include using an encapsulation process, such as molding and/or dispensing the encapsulation layer (e.g., encapsulation layer 132) on the at least one wire bond 313 and/or the sensing chip 304. Additionally, placing and/or forming an encapsulation layer can include encapsulating the adhesive 318 and/or at least one of the contact pads 312 on the sensing chip 304.

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:
1. A sensor assembly, comprising:
    a sensor chip, comprising:
        an array of conductive elements supported on the sensor chip,
        dispense chemistry disposed on at least one conductive element of the array of conductive elements, and
        at least one contact pad disposed on the sensor chip and spaced apart from the array of conductive elements; and
    a microfluidic cap coupled to the sensor chip so that the microfluidic cap and the sensor chip define a first cavity that is located between the microfluidic cap and the sensor chip, the microfluidic cap comprising an electrode coupled to the at least one contact pad of the sensor chip via a conductive adhesive, the conductive adhesive located within the first cavity, the microfluidic cap and the sensor chip define a second cavity that is located between the microfluidic cap and the sensor chip, the second cavity configured to receive a fluid sample, the electrode in electrical communication with the second cavity for measuring an impedance or capacitance of the fluid sample when the fluid sample is present within the second cavity, the measured impedance or capacitance based on an analyte present within the fluid sample.

2. The sensor assembly of claim 1, wherein the electrode is further configured to transmit an electrical signal through a fluid sample to the at least one conductive element.

3. The sensor assembly of claim 1, wherein the sensor chip further comprises at least one bonding pad configured to connect the sensor chip with a printed circuit board, the at least one bonding pad comprising one of: a wire bonding connection or a solder bump connection.

4. The sensor assembly of claim 1, wherein the microfluidic cap comprises one of: a glass material or a polymer material.

5. The sensor assembly of claim 1, wherein the conductive adhesive comprises glass fibers configured to bond the microfluidic cap with the sensing chip.

6. The sensor assembly of claim 1, wherein the array of conducting elements are arranged in an M by N matrix that includes at least one dummy element configured to provide an alternating current (AC) ground.

7. A sensor system, comprising:
a base substrate; and
a sensor assembly coupled to the base substrate, the sensor assembly comprising:
  a sensor chip, comprising:
    an array of conductive elements supported by the sensor chip,
    dispense chemistry disposed on at least one conductive element of the array of conductive elements, and
    at least one contact pad disposed on the sensor chip and spaced apart from the array of conductive elements; and
  a microfluidic cap coupled to the sensor chip so that the microfluidic cap and the sensor chip define a first cavity that is located between the microfluidic cap and the sensor chip, the microfluidic cap comprising an electrode coupled to the at least one contact pad of the sensor chip via a conductive adhesive, the conductive adhesive located within the first cavity, the microfluidic cap and the sensor chip define a second cavity located between the microfluidic cap and the sensor chip, the second cavity configured to receive a fluid sample, the electrode in electrical communication with the second cavity for measuring an impedance or capacitance of the fluid sample when the fluid sample is present within the second cavity, the measured impedance or capacitance based on an analyte present within the fluid sample.

8. The sensor system of claim 7, wherein the electrode is further configured to transmit an electrical signal through a fluid sample to the at least one conductive element.

9. The sensor system of claim 7, wherein the sensor chip further comprises at least one bonding pad configured to connect the sensor chip with a printed circuit board, the at least one bonding pad comprising one of: a wire bonding connection or a solder bump connection.

10. The sensor system of claim 7, further comprising one of:
a spacer bead disposed between the microfluidic cap and the sensor chip and configured to control cavity spacing between the microfluidic cap and the sensor chip or a spacer rod disposed between the microfluidic cap and the sensor chip and configured to control cavity spacing between the microfluidic cap and the sensor chip.

11. The sensor system of claim 7, further comprising:
an encapsulation layer disposed on at least a portion of the sensor chip and the conductive adhesive.

12. A method for fabricating a sensor assembly, comprising:
placing dispense chemistry on at least one conductive element of a sensor chip, wherein the at least one conductive element is part of an array of conductive elements defining a M by N matrix, where M is a number of rows of the array of conductive elements and N is a number of columns of the array of conductive elements, and wherein the sensor chip further comprises at least one contact pad disposed on the sensor chip and spaced apart from the array of conductive elements;
placing a conductive adhesive on the at least one contact pad;
positioning an electrode on a microfluidic cap; and
coupling the electrode of the microfluidic cap to the at least one contact pad of the sensor chip via the conductive adhesive such that the microfluidic cap is positioned over at least a portion of the sensor chip, the microfluidic cap and the sensor chip defining a first cavity that is located between the microfluidic cap and the sensor chip, the conductive adhesive located within the first cavity, the microfluidic cap and the sensor chip define a second cavity that is located between the microfluidic cap and the sensor chip, the second cavity configured to receive a fluid sample.

13. The method for fabricating the sensor assembly of claim 12, further comprising:
allowing dispense chemistry to dry to form a plurality of dispense chemistry islands on the array of conductive elements with a separation distance between different dispense chemistry islands.

14. The method for fabricating the sensor assembly of claim 12, further comprising:
encapsulating at least a portion of the sensor chip and the conductive adhesive with an encapsulation layer.

* * * * *